United States Patent [19]
Picciano

[11] Patent Number: 5,897,872
[45] Date of Patent: Apr. 27, 1999

[54] IODINE-CONTAINING NASAL MOISTURIZING SALINE SOLUTION

[76] Inventor: Dante J. Picciano, 31 Center St., Tamaqua, Pa. 18252

[21] Appl. No.: 08/968,549

[22] Filed: Nov. 12, 1997

[51] Int. Cl.⁶ ..................................................... A61F 13/02
[52] U.S. Cl. ............................................................... 424/434
[58] Field of Search ............................................. 424/434

[56] References Cited

U.S. PATENT DOCUMENTS

| | | |
|---|---|---|
| 4,355,021 | 10/1982 | Mahl et al. . |
| 4,603,131 | 7/1986 | Bernstein et al. . |
| 4,940,728 | 7/1990 | Postley . |
| 5,169,849 | 12/1992 | Kiechel et al. . |
| 5,478,565 | 12/1995 | Geria . |
| 5,508,282 | 4/1996 | Tulin-Silver et al. . |
| 5,562,908 | 10/1996 | Geria . |
| 5,622,724 | 4/1997 | Bryce-Smith . |

*Primary Examiner*—Carlos Azpuru

[57] ABSTRACT

The present invention reveals an iodine-containing nasal moisturizing saline solution and a method for the prevention and/or treatment of sinusitis and related conditions associated with nasal congestion. The nasal moisturizing saline solution is made of water, sodium chloride, iodine, buffer, and a preservative. The iodine-containing nasal moisturizing saline solution is buffered and made isotonic. In the method for the prevention and/or treatment of sinusitis and related conditions associated with nasal congestion, the nasal moisturizing saline solution is administered to the nostrils of a patient in need thereof.

12 Claims, No Drawings

IODINE-CONTAINING NASAL MOISTURIZING SALINE SOLUTION

BACKGROUND OF THE INVENTION

1. Field of the Invention

The present invention discloses an iodine-containing nasal moisturizing saline solution and a method for the prevention and/or treatment of sinusitis and related conditions associated with nasal congestion. The nasal moisturizing saline solution is buffered, isotonic, and contains at least 0.001% iodine by weight. In the method for the prevention and/or treatment of sinusitis and related conditions associated with nasal congestion, the iodine-containing nasal moisturizing saline solution is administered to the nostrils of a patient in need thereof.

2. Description of the Related Art

The nose is a specialized structure that serves dual functions as the organ for the sense of smell and as an entry to the respiratory tract. Nerve receptor cells within the nose detect odors that enter via the nostrils and transmit signals to the brain through the olfactory nerve. The sense of smell also enhances the sense of taste. The ability to smell is more refined than the ability to taste. Therefore, when a cold blocks nasal passages, food may seem bland or even tasteless.

As part of the respiratory tract, the nose moisturizes and warms incoming air and filters out foreign materials. Small glands within the lining of the nose secrete mucus, a sticky substance that lubricates the walls of the nose and throat. Mucus humidifies the incoming air and traps bacteria, dust, and other particles entering the nose. Many bacteria are dissolved by chemical elements in the mucus or transported to the entrance of the throat by the tiny, hairlike structures called cilia. In the throat, bacteria are then swallowed and killed by acids and other chemicals produced in the stomach. This line of defense protects the body against the billions of bacteria that continually enter the nose.

Connected to the nose are sinuses or air-filled cavities located within certain facial bones. There are four groups of sinuses, namely, frontal, sphenoidal, ethmoidal, and maxillary. The sinuses are lined with a mucous membrane and are normally kept clear when mucus drains through them into the nasal passages. If they are obstructed for any reason, such as from the congestion present during a cold, normal drainage cannot occur and infection of the sinuses can result.

Sinusitis and inhalant allergy are two of the most common conditions affecting the nasal passages. Sinusitis is an infection, usually bacterial, of one or more of the sinuses. A sinus infection may be triggered by anything that prevents the mucus in the sinuses from draining properly into the nasal passages. Possible causes include swimming and diving, injuries, abnormal structure of the facial bones, congestion from the flu or a cold, allergies, or an abscess in a tooth which may penetrate the sinuses and allow bacteria to enter them. Many different types of bacteria can cause sinusitis, including some of the same strains that lead to pneumonia, laryngitis, and middle ear infections.

Sinusitis is characterized by pain and tenderness above the infected sinus, which is felt in the face and forehead, behind the eyes, in the eyes, near the upper part of the nose, and even in the upper teeth. This facial pain may be accompanied by headache, slight fever, chills, sore throat, nasal obstruction, and a discharge of pus from the nose.

Sinusitis usually lasts about two weeks, with the pain often subsiding in the morning and worsening as the day goes on, or fluctuating as the patient moves about and changes positions. There is evidence that smokers are more likely to suffer from sinusitis than are nonsmokers. Those who frequently have colds are also more susceptible to sinusitis. Avoiding smoking and exposure to persons with colds may help to prevent sinusitis.

The sinuses cannot be seen directly, so diagnostic evaluation may include X-ray examination to check for the presence of fluid or abnormalities in the sinuses and to determine which of the sinuses are infected. Computed tomography is an excellent tool for evaluating serious sinus problems.

Sinusitis is treated by encouraging drainage of the sinuses. Nasal decongestants, nasal moisturizers, and moist heat work to aid sinus drainage. The nasal moisturizers may be in the form of a nasal spray or nasal drops. In addition, physicians will usually prescribe an antibiotic that will kill the bacteria that most commonly trigger sinusitis.

Inhalant allergens are those that are breathed in, including such substances as dust, pollen, feathers, and animal dander. Hay fever is an inhalant allergy in which the mucous membranes react to various inhaled substances, usually the pollens associated with the changing seasons. Year-round "hay fever" may actually be a reaction to pet dander, feather, mold, or dust.

The symptoms of hay fever are usually the same, regardless of the allergen. Common symptoms include itching of the nose and roof of the mouth; a thin watery discharge constantly draining from the nose; itchy, watery eyes; sneezing; headache; irritability; a feeling of exhaustion; insomnia; loss of appetite; and in advanced cases, coughing and wheezing.

A severe case of hay fever may be best treated by changing the environment, that is by removing the allergen causing the trouble or reducing the patient's exposure to it. Those who react to weed pollen may need to move to a more urban location with a lower concentration of pollen in the air. Many hay fever suffers will benefit from using an air conditioner, which filters the air and thus keeps pollen levels in the home to a minimum. There is no way to prevent hay fever, but avoiding the allergens as much as possible may at least help to relieve some of the discomfort.

Several medications are available for the hay fever sufferer: oral antihistamines, which counteract the histamine that is released by the body in reaction to the allergen; corticosteroids, which reduce inflammation; eye drops, which relieve itching and redness; and desensitization shots, which cause the body to develop tolerance to the allergen. In addition, nasal moisturizers work to aid sinus drainage. The nasal moisturizers may be in the form of a nasal spray or nasal drops.

Several nasal moisturizers are presently commercially available as over-the-counter or non-prescription medications, e.g., Afrin® Moisturizing Saline Mist, Ayr® Saline Nasal Mist, NaSal™ Saline Moisturizer, and Ocean®. Basic nasal moisturizers are made of an aqueous solution of sodium chloride, a preservative, and a buffer.

Numerous examples of nasal solutions, methods of use, and variations thereof have been reported. For example, U.S. Pat. No. 5,622,724 (Bryce-Smith) discloses a method for treating the symptoms of the common cold by administering a spray solution containing a nontoxic, symptom effective treating amount of a solution of a substantially unchelated ionic zinc compound to the nostrils and respiratory tract of a patient.

U.S. Pat. No. 5,562,908 (Geria) discloses nasal compositions effective for relieving mammalian sinus headache associated with inflamed or congested turbinates, containing an anesthetically effective amount of a non-addictive, rapidly absorbable anesthetic component, i.e., an acid addition salt of dyclonine or pramoxine. The anesthetic component is the sole active ingredient in the composition or is combined with a decongestant of the sympathomimetic amine class.

U.S. Pat. No. 5,508,282 (Tulin-Silver et al.) discloses a stable, non-irritating composition and method for treating, without side effects, acute or chronic rhinosinusitis and its associated upper airway symptoms. The composition and treatment are useful for relieving the symptoms, and shortening the duration, of acute or chronic rhinosinusitis. The composition comprises a therapeutically effective solution having a pH of about 6.0, of ascorbic acid and caffeine, in combination with other soluble vitamins, natural ingredients and preservatives in a pharmaceutically acceptable carrier. The method includes the steps of preparing and administering the composition to the nasal membranes of a patient in the form of a nasal spray or drops.

U.S. Pat. No. 5,478,565 (Geria) discloses a topically applicable nasal composition capable of relieving mammalian sinus headache. The composition contains (i) an anesthetically effective amount of an acid addition salt of dyclonine or pramoxine and (ii) an adrenergically effective amount of an acid addition salt of a sympathomimetic amine decongestant selected from the group consisting of an arylalkylamine, imidazoline and a cycloalkylamine incorporated in a pharmaceutically acceptable carrier.

U.S. Pat. No. 5,169,849 (Kiechel et al.) discloses a liquid nasal pharmaceutical composition which contains as an active agent a pharmaceutically effective amount of dihydroergotamine which is capable of depressing the ciliary function and an effective amount of a xanthine which is capable of increasing the ciliary function. The weight ratio of the dihydroergotamine to the xanthine is from 0.1:1 to 10:1.

U.S. Pat. No. 4,940,728 (Postley) discloses a method for treating sino-nasal congestion, viral nasopharyngitis, allergic rhinitis, and related conditions associated with nasal congestion. The method comprises applying to the nasal mucosa a solution comprising ascorbic acid, a pharmaceutically acceptable salt or ester of ascorbic acid, or combinations thereof dissolved in a pharmaceutically acceptable liquid carrier in an amount effective to treat sino-nasal congestion.

U.S. Pat. No. 4,603,131 (Bernstein et al.) discloses a method and composition for preventing irritation of a mucous membrane of the nose caused by allergies, chemical pollutants, or physical irritants manifested by sneezing, discomfort, stuffiness or mucous discharge. The method comprises applying topically to a mucous membrane of the nose a therapeutically effective amount of a tri-cyclic antidepressant.

Iodine is a halogen element of a peculiar odor and acrid taste. Iodine is characterized by the chemical symbol I, has an atomic number of 53, and an atomic weight of 126.904. It is a nonmetallic element, occurring in heavy, grayish black plates or granules. Iodine is essential in nutrition, being especially abundant in the colloid of the thyroid gland. One gram of iodine dissolves in 2950 ml of water or in 12.5 ml alcohol. Internally, iodine is used for treatment of goiter, hyperthyroidism, and as an antidote to alkaloid poisons. Topically, iodine has been used as an antiseptic.

In addition, iodine has been used to destroy viruses. For example, U.S. Pat. No. 4,355,021 discloses a substantially dry, impregnated wipe having iodine and a means for retaining the iodine. The iodine is present in the wipe in an amount from about 1% to about 15% by weight of the wipe and in an amount sufficient to provide virucidal activity. The iodine is preferably present in an amount of from about 2% to about 5%. A flexible paper is preferred, and the most preferred substrate is facial tissue.

However, none of the cited patents disclose a nasal moisturizing solution containing iodine. It is, therefore, an object of this patent application to disclose an iodine-containing nasal moisturizer solution. The iodine-containing nasal moisturizer solution is useful for the prevention and/or treatment of sinusitis, sino-nasal congestion, acute or chronic rhinosinusitis, viral nasopharyngitis, allergic rhinitis, inhalant allergy, and related conditions associated with nasal congestion.

It is a further object of this patent application to disclose a method of use for the iodine-containing nasal moisturizer solution, where the solution is used to prevent and/or treat sinusitis, sino-nasal congestion, acute or chronic rhinosinusitis, viral nasopharyngitis, allergic rhinitis, inhalant allergy, and related conditions associated with nasal congestion.

SUMMARY OF THE INVENTION

The present invention discloses a nasal moisturizing saline solution and a method for the prevention and/or treatment of sinusitis and related conditions associated with nasal congestion.

The nasal moisturizing saline solution is comprised of water; sodium chloride, 0.65% by weight; iodine, at least 0.001% by weight; buffer; and a preservative, where the nasal moisturizing saline solution is buffered and made isotonic.

The iodine is present in the nasal moisturizing saline solution at a concentration between from about 0.001% to about 0.03% by weight. The buffer is selected from the group consisting of sodium bicarbonate, disodium phosphate/sodium phosphate, and monobasic potassium phosphate/sodium hydroxide. The preservative is selected from the group consisting of phenylcarbinol, benzalkonium chloride, and thimerosal.

In a preferred embodiment, the iodine is present in the nasal moisturizing saline solution at a concentration of about 0.02% by weight, the buffer is sodium bicarbonate, and the preservative is phenylcarbinol.

In another preferred embodiment, the iodine is present in the nasal moisturizing saline solution at a concentration of about 0.01% by weight, the buffer is sodium bicarbonate, and the preservative is phenylcarbinol.

In the method for the prevention and/or treatment of sinusitis and related conditions associated with nasal congestion, a nasal moisturizing saline solution is administered to the nostrils of a patient in need thereof. The nasal moisturizing saline solution is comprised of water; sodium chloride, 0.65% by weight; iodine, at least 0.001% by weight; buffer; and a preservative, where the nasal moisturizing saline solution is buffered and made isotonic.

The iodine is present in the nasal moisturizing saline solution at a concentration between from about 0.001% to about 0.03% by weight. The buffer is selected from the group consisting of sodium bicarbonate, disodium phosphate/sodium phosphate, and monobasic potassium phosphate/sodium hydroxide. The preservative is selected from the group consisting of phenylcarbinol, benzalkonium chloride, and thimerosal.

In a preferred embodiment, the iodine is present in the nasal moisturizing saline solution at a concentration of about 0.02% by weight, the buffer is sodium bicarbonate, and the preservative is phenylcarbinol.

In another preferred embodiment, the iodine is present in the nasal moisturizing saline solution at a concentration of about 0.01% by weight, the buffer is sodium bicarbonate, and the preservative is phenylcarbinol.

DETAILED DESCRIPTION OF THE PREFERRED EMBODIMENT

The present invention discloses an iodine-containing nasal moisturizing saline solution and a method for the prevention and/or treatment of sinusitis and related conditions associated with nasal congestion.

In general, the nasal moisturizing saline solution is comprised of pure water; sodium chloride, 0.65% by weight; iodine, at least 0.001% by weight; buffer; and a preservative, where the nasal moisturizing saline solution is buffered and made isotonic. The iodine is present in the nasal moisturizing saline solution at a concentration range of between from about 0.001% to about 0.03% by weight. The buffer is used to maintain physiological pH. Any buffer or buffer system which is capable of maintaining physiological pH may be used. Examples of acceptable buffers and buffer systems include sodium bicarbonate, disodium phosphate/sodium phosphate, and monobasic potassium phosphate/sodium hydroxide. Likewise, any antiseptic preservative which is capable of preserving the sterility of the nasal moisturizing saline solution may be used. Examples of acceptable preservatives include phenylcarbinol, benzalkonium chloride, and thimerosal.

In a preferred embodiment, the iodine is present in the nasal moisturizing saline solution at a concentration of about 0.02% by weight, the buffer is sodium bicarbonate, and the preservative is phenylcarbinol.

In another preferred embodiment, the iodine is present in the nasal moisturizing saline solution at a concentration of about 0.01% by weight, the buffer is sodium bicarbonate, and the preservative is phenylcarbinol.

Since this invention discloses a solution that it administered to the mucous membranes of the nasal passages of a human, it is important to maintain sterile conditions throughout the preparation of the nasal moisturizing saline solution. The following specific Examples are used to illustrate the iodine-containing nasal moisturizing saline solution of the present invention.

A. Nasal Moisturizing Saline Solution

EXAMPLE 1

1.875 fl. oz. (55 ml) of nasal saline solution was purchased commercially over the counter (Phar-Mor, Inc., Youngstown, Ohio). The solution contained purified water, sodium chloride (0.65% by weight), was buffered and made isotonic with sodium bicarbonate, and contained phenylcarbinol as a preservative.

1 fl. oz. (30 ml) of a 2% iodine solution was purchased commercially over the counter (Swan®, Smyrna, Tenn.). The solution contained purified water, 2.4% iodine by weight, and 47% alcohol by volume.

Four (4) drops of the 2% iodine solution was added to the 1.875 fl. oz. (55 ml) of nasal saline solution, thereby yielding a nasal saline solution containing approximately 0.014% by weight iodine.

EXAMPLE 2

1.5 fl. oz. (44 ml) of nasal saline solution was purchased commercially over the counter (Perrigo®, Allegan, Mich.). The solution contained purified water, sodium chloride (0.65% by weight), was buffered and made isotonic with sodium bicarbonate, and contained phenylcarbinol as a preservative.

1 fl. oz. (30 ml) of a 2% iodine solution was purchased commercially over the counter (Swan®, Smyrna, Tenn.). The solution contained purified water, 2.4% iodine by weight, and 47% alcohol by volume.

Five (5) drops of the 2% iodine solution was added to the 1.5 fl. oz. (44 ml) of nasal saline solution, thereby yielding a nasal saline solution containing approximately 0.022% by weight iodine.

EXAMPLE 3

1.5 fl. oz. (45 ml) of Afrin® moisturizing saline mist solution was purchased commercially over the counter (Schering-Plough, Memphis, Tenn.). The solution contained water, PEG-32, sodium chloride, PVP, disodium phosphate, sodium phosphate, benzalkonium chloride, and disodium EDTA.

1 fl. oz. (30 ml) of a 2% iodine solution was purchased commercially over the counter (Swan®, Smyrna, Tenn.). The solution contained purified water, 2.4% iodine by weight, and 47% alcohol by volume.

Three (3) drops of the 2% iodine solution was added to the 1.5 fl. oz. (45 ml) of saline mist solution, thereby yielding a nasal saline solution containing approximately 0.013% by weight iodine.

EXAMPLE 4

1.69 fl. oz. (50 ml) of Ayr® saline nasal mist solution was purchased commercially over the counter (B. F. Ascher & Company, Inc., Lenexa, Kans.). The solution contained deionized water, sodium chloride (0.65% by weight), adjusted to isotonicity and pH with monobasic potassium phosphate/sodium hydroxide buffer, and contained thimerosal and benzalkonium as preservatives.

1 fl. oz. (30 ml) of a 2% iodine solution was purchased commercially over the counter (Swan®, Smyrna, Tenn.). The solution contained purified water, 2.4% iodine by weight, and 47% alcohol by volume.

One (1) drop of the 2% iodine solution was added to the 1.69 fl. oz. (50 ml) of saline mist solution, thereby yielding a nasal saline solution containing approximately 0.004% by weight iodine.

EXAMPLE 5

0.5 fl. oz. (15 ml) of NaSal™ saline moisturizer solution was purchased commercially over the counter (Bayer Corporation, Meyerstown, Pa.). The solution contained purified water, sodium chloride (0.65% by weight), mono- and di-basic sodium phosphates as buffers, and benzalkonium chloride and thimerosal (0.001%) as preservatives.

1 fl. oz. (30 ml) of a 2% iodine solution was purchased commercially over the counter (Swan®, Smyrna, Tenn.). The solution contained purified water, 2.4% iodine by weight, and 47% alcohol by volume.

Two (2) drops of the 2% iodine solution was added to the 0.5 fl. oz. (15 ml) of saline moisturizer solution, thereby yielding a solution containing approximately 0.026% by weight iodine.

B. Method of Administration

In the method for the prevention and/or treatment of sinusitis and related conditions associated with nasal congestion, the iodine-containing nasal moisturizing saline solution is administered to the nostrils of a patient in need thereof. The nasal moisturizing saline solution is comprised of water; sodium chloride, 0.65% by weight; iodine, at least 0.001% by weight; buffer; and a preservative, where the nasal moisturizing saline solution is buffered and made isotonic.

The iodine is present in the nasal moisturizing saline solution at a concentration between from about 0.001% to about 0.03% by weight. The buffer is used to maintain physiological pH. Any buffer or buffer system which is capable of maintaining physiological pH may be used. Examples of acceptable buffers and buffer systems include sodium bicarbonate, disodium phosphate/sodium phosphate, and monobasic potassium phosphate/sodium hydroxide. Likewise, any antiseptic preservative which is capable of preserving the sterility of the nasal moisturizing saline solution may be used. Examples of acceptable preservatives include phenylcarbinol, benzalkonium chloride, and thimerosal.

In a preferred embodiment, the iodine is present in the nasal moisturizing saline solution at a concentration of about 0.02% by weight, the buffer is sodium bicarbonate, and the preservative is phenylcarbinol.

In another preferred embodiment, the iodine is present in the nasal moisturizing saline solution at a concentration of about 0.01% by weight, the buffer is sodium bicarbonate, and the preservative is phenylcarbinol.

The iodine-containing nasal moisturizing saline solution may be applied to the mucous membranes of the nose by using nose drops or a nose spray. Before using nose drops or sprays, the patient should gently blow his/her nose if he/she can. For the administration of the nose drops, the patient should fill the dropper, tilt his/her head back, and place the prescribed number of drops into his/her nose. To prevent contamination of the rest of the solution, the dropper should not touch the nasal membranes. The patient should keep his/her head titled for five to ten seconds, and sniff gently two or three times.

When using a nasal spray, however, the patient should not tilt his/her head back. The sprayer should be inserted into the nose, but without touching the inner nasal membranes. The patient should sniff and squeeze the sprayer at the same time. The patient should not release his/her grip on the sprayer until it has been withdrawn from the nose in order to prevent nasal mucus and bacteria from entering the plastic bottle and contaminating its contents. After the patient has sprayed the prescribed number of times in one or both nostrils, he/she should gently sniff two or three times.

The following specific Examples are used to illustrate the method for the prevention and/or treatment of sinusitis and related conditions associated with nasal congestion of the present invention.

EXAMPLE 6

Patient 1 was a fifty-two year old male who suffered sinusitis, sino-nasal congestion, rhinosinusitis, and inhalant allergy for several years. He began to use the nasal moisturizing saline solution disclosed in Example 1. Each morning he would spray the nasal moisturizing saline solution into each nostril. The process was repeated so that each nostril was sprayed twice. He would then gently blow his nose of excess nasal moisturizing saline solution.

After the initial application of the nasal moisturizing saline solution, a mild stinging sensation of the mucous membranes was noted. The sensation diminished with each subsequent application each morning, so that by day four there was no longer any mild stinging sensation associated with the application of the solution. Thereafter, Patient 1 reported that the severity of his sinusitis, sino-nasal congestion, rhinosinusitis, and inhalant allergy diminished greatly.

Patient 1 continued daily applications for twelve months and reported that the frequency of sinusitis, sino-nasal congestion, rhinosinusitis, and inhalant allergy episodes diminished greatly. Patient 1 continues to apply the nasal moisturizing saline solution of Example 1 to each nostril daily.

EXAMPLE 7

Patient 2 was a forty-two year old male who suffered sinusitis, sino-nasal congestion, and rhinosinusitis, for several years. He began to use the nasal moisturizing saline solution disclosed in Example 2. Each morning he would spray the nasal moisturizing saline solution into each nostril. The process was repeated so that each nostril was sprayed twice. He would then gently blow his nose of excess nasal moisturizing saline solution.

After the initial application of the nasal moisturizing saline solution, Patient 2 noted a mild stinging sensation of the mucous membranes. The sensation diminished with each subsequent application each morning, so that by day three there was no longer any mild stinging sensation associated with the application of the solution. Thereafter, Patient 2 reported that the severity of his sinusitis, sino-nasal congestion, and rhinosinusitis diminished greatly.

Patient 2 continued daily applications for six months and reported that the frequency of sinusitis, sino-nasal congestion, and rhinosinusitis episodes diminished greatly. Patient 2 continues to apply the nasal moisturizing saline solution of Example 2 to each nostril daily.

The exact mechanism of action of the nasal moisturizing saline solution for successfully treating and/or preventing sinusitis, sino-nasal congestion, acute or chronic rhinosinusitis, viral nasopharyngitis, allergic rhinitis, inhalant allergy, and related conditions associated with nasal congestion is unknown.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A nasal moisturizing saline solution, comprising:
   a) water,
   b) sodium chloride, 0.65% by weight,
   c) iodine, at least 0.001% by weight,
   d) buffer, and
   e) a preservative,
   wherein the nasal moisturizing saline solution is buffered and made isotonic.

2. The nasal moisturizing saline solution of claim 1, wherein the iodine is present in the solution at a concentration between from about 0.001% to about 0.03% by weight.

3. The nasal moisturizing saline solution of claim 1, wherein the buffer is selected from the group consisting of sodium bicarbonate, disodium phosphate/sodium phosphate, and monobasic potassium phosphate/sodium hydroxide.

4. The nasal moisturizing saline solution of claim 1, wherein the preservative is selected from the group consisting of phenylcarbinol, benzalkonium chloride, and thimerosal.

5. The nasal moisturizing saline solution of claim 1, wherein the iodine is present in the solution at a concentration of about 0.02% by weight, the buffer is sodium bicarbonate, and the preservative is phenylcarbinol.

6. The nasal moisturizing saline solution of claim 1, wherein the iodine is present in the solution at a concentration of about 0.01% by weight, the buffer is sodium bicarbonate, and the preservative is phenylcarbinol.

7. A method for the prevention and/or treatment of sinusitis and related conditions associated with nasal congestion, comprising administering a nasal moisturizing saline solution to the nostrils of a patient in need thereof, wherein the nasal moisturizing saline solution comprises:

a) water,
   b) sodium chloride, 0.65% by weight,
   c) iodine, at least 0.001% by weight,
   d) buffer, and
   e) a preservative,
   wherein the nasal moisturizing saline solution is buffered and made isotonic.

8. The method of claim 7, wherein the iodine is present in the solution at a concentration between from about 0.001% to about 0.03% by weight.

9. The method of claim 7, wherein the buffer is selected from the group consisting of sodium bicarbonate, disodium phosphate/sodium phosphate, and monobasic potassium phosphate/sodium hydroxide.

10. The method of claim 7, wherein the preservative is selected from the group consisting of phenylcarbinol, benzalkonium chloride, and thimerosal.

11. The method of claim 7, wherein the iodine is present in the solution at a concentration of about 0.02% by weight, the buffer is sodium bicarbonate, and the preservative is phenylcarbinol.

12. The method of claim 7, wherein the iodine is present in the solution at a concentration of about 0.01% by weight, the buffer is sodium bicarbonate, and the preservative is phenylcarbinol.

* * * * *